(12) United States Patent
Longchambon et al.

(10) Patent No.: US 8,987,361 B2
(45) Date of Patent: Mar. 24, 2015

(54) ORGANOSILANE COUPLING AGENT

(75) Inventors: Karine Longchambon, Beaumont (FR); José Carlos Araujo Da Silva, Pont Du Chateau (FR); Nicolas Seeboth, Clermont-Ferrand (FR); Sergey Ivanov, Orekhovo-Zouevo (FR)

(73) Assignees: Michelin Recherche et Technique S.A., Granges-Paccot (CH); Compagnie Generale des Etablissements Michelin, Clermont-Ferrand (FR)

( * ) Notice: Subject to any disclaimer, the term of this patent is extended or adjusted under 35 U.S.C. 154(b) by 446 days.

(21) Appl. No.: 13/321,825

(22) PCT Filed: May 20, 2010

(86) PCT No.: PCT/EP2010/003117
§ 371 (c)(1),
(2), (4) Date: Mar. 7, 2012

(87) PCT Pub. No.: WO2010/133373
PCT Pub. Date: Nov. 25, 2010

(65) Prior Publication Data
US 2012/0165468 A1 Jun. 28, 2012

(30) Foreign Application Priority Data
May 20, 2009 (FR) ...................................... 09 02452

(51) Int. Cl.
*C08K 5/24* (2006.01)
*C07F 7/08* (2006.01)
(52) U.S. Cl.
CPC .................................. *C07F 7/0836* (2013.01)
USPC ........................... 524/262; 525/102; 556/427

(58) Field of Classification Search
CPC ......... C07F 7/081; C08L 83/00; C08L 83/06; C08L 83/08; C09C 1/28
USPC ............................. 524/262; 525/102; 556/427
See application file for complete search history.

(56) References Cited

FOREIGN PATENT DOCUMENTS

| EP | 0 964 021 | 12/1999 |
|---|---|---|
| WO | WO 99/02601 | 1/1999 |
| WO | WO 03/054075 | 7/2003 |
| WO | WO 03/097734 | 11/2003 |

OTHER PUBLICATIONS

Database Registry "Chemical Abstracts Service, Columbus, Ohio, US" Jun. 13, 2002 XP002558915.*
Xia et al. "Functionalized Polyethylene glycol)—Grafted Polysiloxane Monolayers for Control of Protein Binding", Sep. 11, 2001, pp. 3255-3262.
Cerveau et al. "Synthesis, Characterization, and Polyeondensation of New Stable α,ω-organo(bis-silanediols)", 2003, pp. 1213-1221.

* cited by examiner

*Primary Examiner* — Edward Cain
(74) *Attorney, Agent, or Firm* — Cozen O'Connor

(57) ABSTRACT

An organosilane of general formula I below: $(HO)_2R^1Si-Z-S_m-R^2$ in which: $R^1$, which are identical or different, each represent a monovalent hydrocarbon-based group chosen from alkyls, which are linear or branched, cycloalkyls or aryls, having from 1 to 18 carbon atoms; $R^2$ represents a monovalent hydrocarbon-based group chosen from alkyls, which are linear or branched, cycloalkyls or aryls, having from 1 to 30 carbon atoms; Z represents a divalent bonding group comprising from 1 to 18 carbon atoms; and m is a number greater than or equal to 2.

13 Claims, No Drawings

ORGANOSILANE COUPLING AGENT

RELATED APPLICATIONS

This is a U.S. national stage of application No. PCT/EP2010/003117, filed on 20 May 2010. Priority is claimed based on French Application No. 09/02452, filed 20 May 2009, the content of which is hereby incorporated herein by reference.

FIELD OF THE INVENTION

The present invention relates to organosilane coupling agents, which can be used, in particular, for coupling reinforcing inorganic fillers and diene elastomers in rubber compositions intended, for example, for the manufacture of tires.

BACKGROUND OF THE INVENTION

It is generally known that in order to obtain the optimum reinforcing properties imparted by a filler, this filler should be present in the elastomer matrix in a final form that is both as finely divided as possible and as uniformly distributed as possible. However, such conditions can be achieved only if the filler has a very good capacity, on the one hand, to be incorporated into the matrix during the mixing with the elastomer and to deagglomerate, and, on the other hand, to disperse uniformly in this matrix.

As is well known, carbon black exhibits such capacities, which is not generally the case for inorganic fillers. Indeed, for reasons of mutual affinities, the inorganic filler particles have an annoying tendency to agglomerate together in the elastomer matrix. These interactions have the harmful consequence of limiting the dispersion of the filler and thus of limiting the reinforcing properties to a level that is substantially below that which it would theoretically be possible to achieve if all the bonds (inorganic filler/elastomer) capable of being created during the compounding operation were actually obtained. Moreover, these interactions tend to increase the consistency in the uncured state of the rubber compositions, and thus to render the processing ("processability") thereof more difficult than in the presence of carbon black.

Ever since savings in fuel and the need to protect the environment have become a priority, it has however proved necessary to produce tires that have a reduced rolling resistance without having a disadvantageous effect on their wear resistance. This has been made possible in particular by virtue of the discovery of novel rubber compositions reinforced with specific inorganic fillers that are described as "reinforcing" and that are capable of competing, from a reinforcing viewpoint, with a conventional tyre-grade carbon black, while giving these compositions a lower hysteresis, synonymous with a lower rolling resistance for the tires comprising them.

Such rubber compositions, comprising reinforcing inorganic fillers of the siliceous or aluminous type, have, for example, been described in the patents or patent applications EP-A-0501227 (or U.S. Pat. No. 5,227,425), EP-A-0735088 (or U.S. Pat. No. 5,852,099), EP-A-0810258 (or U.S. Pat. No. 5,900,449), EP-A-0881252, WO99/02590, WO99/02601, WO99/02602, WO99/28376, WO00/05300 and WO00/05301.

Mention will be made in particular of documents EP-A-0501227, EP-A-0735088 or EP-A-0881252 which disclose diene rubber compositions reinforced with highly dispersible precipitated silicas, such compositions making it possible to manufacture treads having a substantially improved rolling resistance, without adversely affecting the other properties, in particular the grip, endurance and wear resistance properties. Such compositions exhibiting such a compromise of contradictory properties are also described in applications EP-A-0810258 and WO99/28376, with, as reinforcing inorganic fillers, specific, highly dispersible aluminous fillers (aluminas or aluminium (oxide)hydroxides), or else in applications WO00/73372 and WO00/73373, which describe specific titanium oxides of reinforcing type.

The use of these specific, highly dispersible inorganic fillers, whether as the predominant reinforcing filler or not, has certainly reduced the difficulties in processing rubber compositions containing them, but this processing nevertheless remains more difficult than for rubber compositions conventionally filled with carbon black.

In particular, it is necessary to use a coupling agent, also referred to as a bonding agent, the role of which is to provide the bonding between the surface of the inorganic filler particles and the elastomer, while facilitating the dispersion of this inorganic filler within the elastomer matrix.

It is recalled here that the expression "coupling agent" (inorganic filler/elastomer coupling agent) is understood, in a known manner, to mean an agent capable of establishing a sufficient bond, of chemical and/or physical nature, between the inorganic filler and the diene elastomer; such a coupling agent, which is at least bifunctional, has, for example, a simplified general formula "Y—W—X", in which:

Y represents a functional group ("Y" function) which is capable of bonding physically and/or chemically to the inorganic filler, such a bond possibly being established, for example, between a silicon atom of the coupling agent and the surface hydroxyl (OH) groups of the inorganic filler (for example, the surface silanols when it is silica);

X represents a functional group ("X" function) capable of bonding physically and/or chemically to the diene elastomer, for example via a sulphur atom; and W represents a divalent group allowing Y to be linked to X.

The coupling agents in particular must not be confused with simple agents for covering the inorganic filler which, in a known manner, may comprise the Y function that is active with respect to the inorganic filler but are devoid of the X function that is active with respect to the diene elastomer.

Coupling agents, in particular silica/diene elastomer coupling agents, have been described in a large number of documents, the most well known being bifunctional organosilanes bearing at least one alkoxyl function as the Y function, and, as the X function, at least one function capable of reacting with the diene elastomer such as for example a sulphurated (i.e., sulphur-containing) function.

Thus, it has been proposed in patent applications FR-A-2094859 or GB-A-1310379 to use a mercaptoalkoxysilane coupling agent for manufacturing tyre treads. It was rapidly demonstrated and it is today well known that mercaptoalkoxysilanes are capable of providing excellent silica/elastomer coupling properties, but that the industrial use of these coupling agents is not possible due to the very high reactivity of sulphurated functions of thiol —SH type (X functions) that very rapidly result, during the preparation of rubber compositions in an internal mixer, in premature vulcanizations also referred to as "scorching", in very high viscosities in the uncured state, and ultimately in rubber compositions that are almost impossible to work and to process industrially. To illustrate this problem, mention may be made, for example, of documents FR-A-2206330, U.S. Pat. No. 3,873,489 and U.S. Pat. No. 4,002,594.

To overcome this drawback, it has been proposed to replace these mercaptoalkoxysilanes with alkoxysilane polysulphides, especially bis(alkoxylsilylpropyl)polysulphides as described in very many documents (see, for example, FR-A-2149339, FR-A-2206330, U.S. Pat. No. 3,842,111, U.S. Pat. No. 3,873,489, U.S. Pat. No. 3,997,581, EP-A-680997 or U.S. Pat. No. 5,650,457, EP-A-791622 or U.S. Pat. No. 5,733,963, DE-A-19951281 or EP-A-1043357 and WO00/53671). Among these polysulphides, mention should especially be made of bis(3-triethoxysilyl-propyl)tetrasulphide (abbreviated to TESPT) and bis(3-triethoxysilylpropyl)disulphide (abbreviated to TESPD).

These alkoxysilane polysulphides, in particular TESPT, are generally considered to be the products that provide, for vulcanizates comprising a reinforcing inorganic filler, in particular silica, the best compromise in terms of scorch safety, ease of processing and reinforcing power. They are, in this respect, the most widely used coupling agents today in rubber compositions for tires, even though they are relatively expensive and, furthermore, must most often be used in a relatively large amount.

SUMMARY OF THE INVENTION

The Applicants have found in the course of their research novel coupling agents of organosilane type which make it possible, surprisingly, in particular compared to the aforementioned alkoxysilane polysulphides, to improve very markedly the processability, in the uncured state, of compositions comprising them, and also the scorch safety.

Thus, one subject aspect of the invention is directed to an organosilane of general formula I below:

$$(HO)_2R^1Si-Z-S_m-R^2$$

in which:
- $R^1$, which are identical or different, each represent a monovalent hydrocarbon-based group chosen from alkyls, which are linear or branched, cycloalkyls or aryls, having from 1 to 18 carbon atoms;
- $R^2$ represents a monovalent hydrocarbon-based group chosen from alkyls, which are linear or branched, cycloalkyls or aryls, having from 1 to 30 carbon atoms;
- Z represents a divalent bonding group comprising from 1 to 18 carbon atoms; and
- m is a number greater than or equal to 2.

Another aspect of the invention is directed a process for obtaining an organosilane of general formula (I) comprising the following steps:
- added to a diazodicarboxylate is a mercaptan of formula (II):

$$R^2-SH,$$

in which $R^2$ has the same meaning as in formula (I), in order to form a thiohydrazine,

- the thiohydrazine obtained is substituted with a second mercaptan of formula (III):

$$(R^3O)_2R^1Si-Z-SH,$$

in which:
- $R^1$ and Z have the same meaning as in formula (I),
- $R^3$, which are identical or different, represent a monovalent hydrocarbon-based group chosen from alkyls having from 1 to 6 carbon atoms, preferably having from 1 to 3 carbon atoms, a hydrolysis is carried out in an acid medium that makes it possible to result in the targeted organosilane of formula (I).

An organosilane of general formula (I) mentioned above can be used as a coupling agent, in particular as an inorganic filler/diene elastomer coupling agent in a rubber composition, and more particularly still in a zinc-free rubber composition.

Indeed, it has been observed, quite surprisingly, that an organosilane in accordance with the invention, used as a coupling agent in rubber compositions, made it possible to very significantly decrease the zinc of rubber formulations reinforced with an inorganic filler such as silica, or even to eliminate it completely, without replacing the zinc with another metal and while protecting the rubber compositions from the problem of premature scorching during the industrial processing thereof. This result proves to be all the more surprising since the TESPT coupling agent is not suitable for compositions that are zinc-free or almost zinc-free.

Indeed, it is recalled that one medium-term objective of tyre manufacturers is to eliminate zinc or its derivatives from their rubber formulations, due to the known, relatively toxic nature of these compounds, especially with respect to water and aquatic organisms (classification R50 according to European Directive 67/548/EEC of 9 Dec. 1996).

However, the elimination of zinc oxide, specifically from rubber formulations reinforced with an inorganic filler such as silica, is highly detrimental to the processing characteristics ("processability") of the rubber compositions in the uncured state, with a reduction in the scorch time that is unacceptable from an industrial point of view.

I. MEASUREMENTS AND TESTS USED

The rubber compositions in which the organosilanes are tested as coupling agent are characterized, before and after curing, as indicated below.

I-1. Mooney Plasticity

Use is made of an oscillating consistometer as described in French Standard NF T 43-005 (1991). The Mooney plasticity measurement is carried out according to the following principle: the composition in the uncured state (i.e., before curing) is moulded in a cylindrical chamber heated to 100° C. After preheating for one minute, the rotor rotates within the test specimen at 2 rpm and the working torque for maintaining this movement is measured after rotating for 4 minutes. The Mooney plasticity (ML 1+4) is expressed in "Mooney unit" (MU, with 1 MU=0.83 Newton.meter).

I-2. Scorch Time

The measurements are carried out at 130° C., in accordance with French Standard NF T 43-005. The change in the consistometric index as a function of time makes it possible to determine the scorch time of the rubber compositions, assessed in accordance with the abovementioned standard, by the parameter T5 (case of a large rotor), expressed in minutes, and defined as being the time necessary to obtain an increase in the consistometric index (expressed in MU) of 5 units above the minimum value measured for this index.

I-3. Dynamic Properties

The dynamic properties $\Delta G^*$ and $\tan(\delta)_{max}$ are measured on a viscosity analyser (Metravib VA4000), in accordance with Standard ASTM D 5992-96. The response of a sample of vulcanized composition (cylindrical test specimen with a thickness of 4 mm and with a cross section of 400 mm²), subjected to a sinusoidal stress in simple alternating shear, at a frequency of 10 Hz, under normal temperature conditions (23° C.), is recorded in accordance with Standard ASTM D 1349-99. A scan with a strain amplitude ranging from 0.1 to 50% (forward cycle) then from 50% to 0.1% (return cycle) is carried out. The results made use of are the complex dynamic shear modulus (G*) and the loss factor (tan δ). For the return cycle, the maximum value of tan δ observed ($\tan(\delta)_{max}$), and also the difference in the complex modulus (ΔG*) between the values at 0.1% and 50% strain (the Payne effect) are indicated.

II. DETAILED DESCRIPTION

II1. Organosilane of the Invention

The first subject aspect of the invention is an organosilane of general formula (I) below:

$$(HO)_2R^1Si-Z-S_m-R^2$$

in which:
- $R^1$, which are identical or different, each represent a monovalent hydrocarbon-based group chosen from alkyls, which are linear or branched, cycloalkyls or aryls, having from 1 to 18 carbon atoms;
- $R^2$ represents a monovalent hydrocarbon-based group chosen from alkyls, which are linear or branched, cycloalkyls or aryls, having from 1 to 30 carbon atoms;
- Z represents a divalent bonding group comprising from 1 to 18 carbon atoms; and
- m is a number greater than or equal to 2, m is an integer or a fraction.

Z may contain one or more heteroatoms chosen from O, S and N.

Preferably m is equal to 2.

Advantageously:
- $R^1$ is chosen from methyl, ethyl, n-propyl and isopropyl, preferably from methyl and ethyl;
- Z is chosen from $C_1$-$C_{18}$ alkylenes and $C_6$-$C_{12}$ arylenes.

According to one embodiment, Z is chosen from $C_1$-$C_{10}$ alkylenes and more preferably Z is chosen from $C_1$-$C_4$ alkylenes.

According to another embodiment, $R^1$ is a methyl.

Preferably $R^2$ is chosen from alkyls having from 1 to 18 carbon atoms, and more preferably still $R^2$ is an octyl.

Mention will in particular be made of (3-(octyldisulphanyl)propyl)methylsilanediol, the formula (I)° of which is such that m is equal to 2, $R^1$ is a methyl, Z is a propylene and $R^2$ is an octyl.

II-2 Synthesis Process

The synthesis process in accordance with another aspect of the invention, for obtaining an organosilane of formula (I) described in detail above, comprises the following steps:
- added to a diazodicarboxylate is a mercaptan of formula (II):

$$R^2-SH,$$

in which $R^2$ has the same meaning as in formula (I),
in order to form a thiohydrazine,
the thiohydrazine obtained is substituted with a second mercaptan of formula (III):

$$(R^3O)_2R^1Si-Z-SH,$$

in which:
- $R^1$ and Z have the same meaning as in formula (I),
- $R^3$, which are identical or different, represent a monovalent hydrocarbon-based group chosen from alkyls having from 1 to 6 carbon atoms, preferably having from 1 to 3 carbon atoms,
a hydrolysis is carried out in an acid medium that makes it possible to result in the targeted organosilane of formula (I).

It should be noted that a person skilled in the art knows how to add sulphur to the organosilane disulphide thus obtained to enable it to pass from $S_2$ to $S_x$ where x is greater than 2.

II-3 Use as a Coupling Agent

As indicated above, the compound of the invention, by virtue of its dual functionality, finds an advantageous industrial application as a coupling agent, intended for example to provide the bonding or adhesion between a reactive polymer matrix (especially a rubber matrix) and any material with a hydroxylated surface, especially a mineral (for example, a glass fibre) or metallic (for example, a carbon steel or stainless steel wire) surface.

Without this being limiting, it may be used for coupling reinforcing inorganic or white fillers and diene elastomers, for example in rubber compositions intended for the manufacture of tires. The expression "reinforcing inorganic filler" is understood, in a known manner, to mean an inorganic or mineral filler, whatever its colour and its origin (natural or synthetic), also known as "white filler" or sometimes "clear filler", in contrast to carbon black, this inorganic filler being capable of reinforcing by itself alone, without means other than an intermediate coupling agent, a rubber composition intended for the manufacture of tires, in other words capable of replacing, in its reinforcing role, a conventional tyre-grade carbon black filler.

For such a use, the diene elastomer is then preferably chosen from the group of highly unsaturated diene elastomers consisting of polybutadienes (BRs), synthetic polyisoprenes (IRs), natural rubber (NR), butadiene-styrene copolymers (SBRs), butadiene-isoprene copolymers (BIRs), butadiene-acrylonitrile copolymers (NBRs), isoprene-styrene copolymers (SIRs), butadiene-styrene-isoprene copolymers (SBIRs) and mixtures of these elastomers.

When the monohydroxysilane of the invention is intended for (inorganic filler/diene elastomer) coupling in a rubber composition forming, for example, all or part of a passenger vehicle tyre tread, the diene elastomer is then preferably an SBR or a blend (mixture) of SBR and of another diene elastomer such as BR, NR or IR. In the case of an SBR elastomer, use is especially made of an SBR having a styrene content between 20% and 30% by weight, a content of vinyl bonds of the butadiene part of between 15% and 65%, a content of trans-1,4-bonds of between 15% and 75% and a glass transition temperature ($T_g$—measured according to the standard ASTM D3418-82) of between −20° C. and −55° C., this SBR copolymer, preferably prepared in solution (SSBR), optionally being used as a mixture with a polybutadiene (BR) preferably having more than 90% of cis-1,4-bonds.

When the tread is intended for a utility vehicle tyre, such as a heavy vehicle tyre, the diene elastomer is then preferably an isoprene elastomer, that is to say a diene elastomer chosen from the group consisting of natural rubber (NR), synthetic polyisoprenes (IRs), various isoprene copolymers and mixtures of these elastomers; it is then more preferably natural rubber or a synthetic polyisoprene of cis-1,4-type having a content (mol %) of cis-1,4-bonds of greater than 90%, more preferably still of greater than 98%.

The organosilanes of the invention have proved sufficiently effective by themselves for coupling a diene elastomer and a reinforcing inorganic filler such as silica, used at a preferred content of greater than 1 phr (parts by weight per hundred parts of elastomer), more preferably between 2 and 20 phr. They may advantageously constitute the sole coupling agent present in rubber compositions reinforced with inorganic filler and intended for the manufacture of tires.

As reinforcing inorganic filler, mention will be made of mineral fillers of siliceous type, in particular silica ($SiO_2$), or of aluminous type, in particular alumina ($Al_2O_3$) or aluminium (oxide) hydroxides, or else reinforcing titanium oxides, as described in the aforementioned patents or patent applications.

III. EXEMPLARY EMBODIMENTS OF THE INVENTION

In the following tests, the invention is performed with a particular organosilane in accordance with the invention: (3-(octyldisulfanyl)propyl)methylsilanediol.

III-1 Synthesis of (3-(octyldisulphanyl)propyl)methylsilanediol

The synthesis is carried out according to the following reaction scheme:

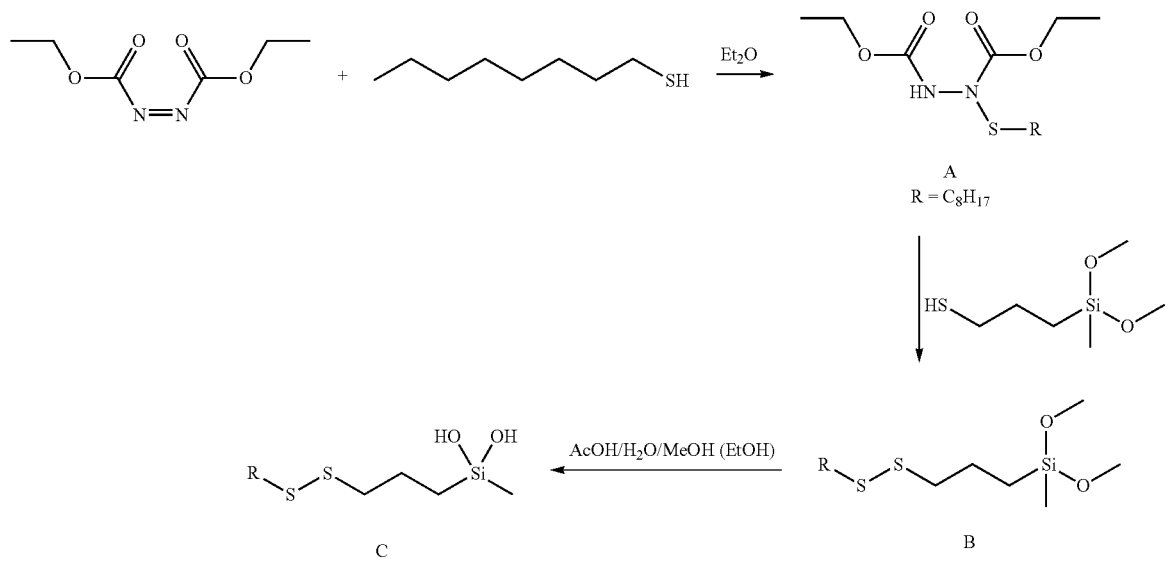

a) Synthesis of Compound A b) Synthesis of Compound B

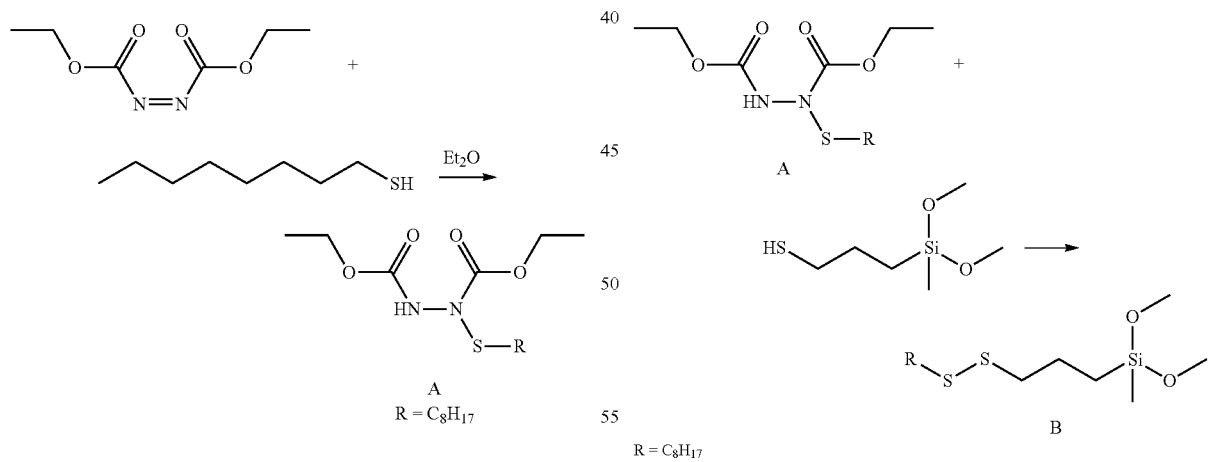

The solution of octanethiol (45.0 g, 0.308 mol) in diethyl ether (250 mL) is added dropwise over 15 minutes to a solution of diethylazodicarboxylate (DEAD with CAS number [1972-28-7] (51.0 g, 0.293 mol) in diethyl ether (100 mL) kept at −22° C. The temperature of the reaction medium remains between −20 and −25° C. The reaction medium is then stirred for 10-15 minutes at a temperature between −20 and −25° C. and for 1.0-1.5 hours at room temperature. After evaporating the solvents under reduced pressure (Tbath 21° C., 11 mbar), petroleum ether (400 mL, 40-60° C. fraction) is added and the mixture is cooled to −18° C. The precipitate of diethyl hydrazodicarboxylate (10.4 g) is filtered and is washed twice with cold petroleum ether (2×20 mL at −18° C.). After evaporating the solvents under reduced pressure (Tbath 23° C., 70 mbar) the product A is obtained in the form of a red oil. An additional purification by chromatography on a silica column (elution gradient: petroleum ether/ethyl acetate, 10/1 to 2/1) makes it possible to collect the product A in the form of a colourless oil (58.3 g, 0.173 mol) with a yield of 59%. The molar purity estimated by $^1$H NMR is greater than 90%.

3-Mercaptopropyldimethoxymethysilane (42.4 g, 0.235 mol) is added to compound B (57.9 g, 0.181 mol). The reaction is exothermic. The reaction medium is then stirred for 2.0-3.5 hours at 120° C. After cooling, petroleum ether (550 mL, 40-60° C. fraction) is added. The mixture is cooled to −18° C. over 12 hours. The precipitate of diethyl hydrazodicarboxylate (28.9 g, 91% yield) is filtered and is washed twice with petroleum ether (2×20 mL, 40-60° C. fraction, −18° C.). After evaporating the solvents under reduced pressure (Tbath 45° C., 12 mbar) the oil obtained is distilled under vacuum (the fraction collected has a boiling point between 98° C. ($3.0 \times 10^{-2}$ mbar) and 102° C. ($4.3 \times 10^{-2}$ mbar)). The product B (53.8 g, 0.167 mol) is obtained in the form of a colourless oil with a yield of 92%. The molar purity estimated by $^1$H and $^{29}$Si NMR is greater than 96% (the remaining 4% being composed of the product A that has not reacted).

c) Synthesis of Compound C

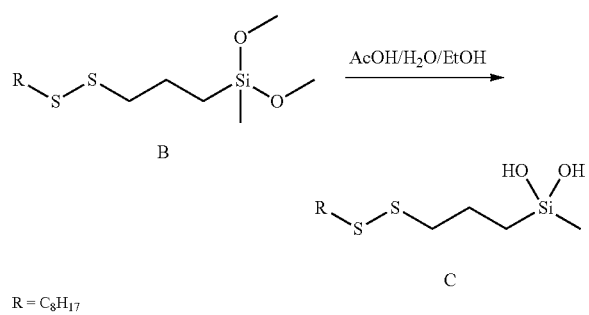

R = $C_8H_{17}$

Compound B (53.0 g, 0.163 mol) is added to a mixture of 0.5% acetic acid, water (105 mL) and ethanol (530 mL). The solution is stirred for 2-3 hours at room temperature then the mixture is poured into water (3600 mL). The product is extracted with diethyl ether (3×300 mL). After evaporating the solvents under reduced pressure (Tbath 21° C.), the oil obtained (60 g) is recrystallized in petroleum ether (850 mL, 40-60° C. fraction) at −20° C. over 12 to 15 hours. The crystals (30.1 g) are filtered, washed with petroleum ether (2×80 mL, −18° C.) and then dried for 2 to 3 hours under reduced pressure. After evaporating the filtrate down to 200-250 mL under reduced pressure (Tbath 21° C.) and crystallization at −20° C. for 2 to 3 hours, the additional crystals (5.4 g) are filtered, washed with petroleum ether (2×25 mL, −18° C.) and then dried for 2 to 3 hours under reduced pressure.

The two fractions are combined then recrystallized in a mixture of petroleum ether (580 mL, 40-60° C. fraction), Et$_2$O (230 mL) for 12 hours. After filtering, washing with petroleum ether (2×60 mL, −18° C.) then evaporating the residual solvents under reduced pressure for 2-3 hours, the product C (30.1 g, 0.101 mol) is obtained with a yield of 62% in the form of a white solid having a melting point of 57° C. The molar purity estimated by $^1$H and $^{29}$Si NMR is greater than 98%.

The yield may be brought to 70% by a supplementary crystallization of the mother liquors.

III-2 Preparation of the Rubber Compositions

The tests which follow are carried out in the following way: the diene elastomer (SBR and BR blend), the silica, supplemented with a small amount of carbon black, the coupling agent and then, after kneading for one to two minutes, the various other ingredients, with the exception of the vulcanization system, are introduced into an internal mixer, 70% filled and having an initial vessel temperature of approximately 90° C. Thermomechanical working (non-productive phase) is then carried out in one stage (total duration of the kneading equal to approximately 5 min) until a maximum "dropping" temperature of approximately 165° C. is reached. The mixture thus obtained is recovered and cooled and then the covering agent (when the latter is present) and the vulcanization system (sulphur and sulphenamide accelerator) are added on an external mixer (homofinisher), at 50° C., the combined mixture being mixed (productive phase) for approximately 5 to 6 min.

The compositions thus obtained are subsequently calendered, either in the form of sheets (thickness of 2 to 3 mm) or of thin films of rubber, for the measurement of their physical or mechanical properties, or in the form of profiled elements which can be used directly, after cutting and/or assembling to the desired dimensions, for example as semi-finished products for tires, in particular as tyre treads.

III-3 Characterization of the Rubber Compositions

III-3.1 Test 1

The purpose of this test is to demonstrate the improved properties of a "standard" rubber composition comprising an organosilane in accordance with the invention as coupling agent; the word standard is understood here to mean the fact that the compositions comprise a vulcanization system customarily used in rubber compositions for tires, compared with rubber compositions that are "standard" rubber compositions but that use coupling agents conventionally used in rubber compositions for tyre treads having silica as the reinforcing filler.

For this, three compositions based on a diene elastomer (SBR/BR blend), reinforced with a highly dispersible silica (HDS) are prepared, these compositions differing essentially in the following technical characteristics:

composition C1 is a control "standard" composition containing the compound TESPT (trade name: "Si69") as coupling agent, composition C2 is a "standard" composition containing the compound TESPD (trade name: "Si266") as coupling agent, "standard" composition C3 comprises an organosilane in accordance with the invention: (3-(octyldisulphanyl) propyl)methylsilanediol, as coupling agent.

In order for the properties of compositions C1 to C3 to be comparable, the coupling agents of compositions C2 to C3 are used at a content that is isomolar in silicon compared to the control composition C1.

The conventional coupling agent used in the control composition C1 is TESPT. It is recalled that TESPT is bis(3-triethoxysilylpropyl)tetrasulphide having the structural formula (Et=ethyl):

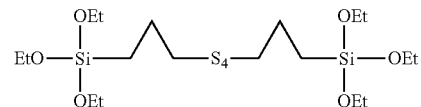

The coupling agent used in composition C2 is TESPD, which is bis(3-triethoxysilyl-propyl)disulphide and therefore closer to the coupling agent in accordance with the invention: (3-(octyldisulphanyl)propyl)methylsilanediol since it is also a disulphide. TESPD has the following formulation:

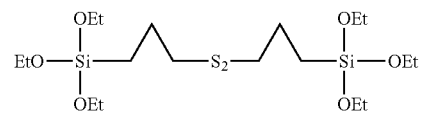

Tables 1 and 2 give the formulation of the various compositions (Table 1—content of the various products expressed in phr or parts by weight per hundred parts of elastomer) and also their properties before and after curing (around 40 min at 150° C.); the vulcanization system consists of sulphur and sulphonamide.

Examination of the results from Table 2 regarding the properties before curing firstly shows, compared to the control composition C1, that only composition C3 comprising, as coupling agent, an organosilane of general formula (I) in accordance with the invention, makes it possible both to improve the scorch safety (scorch time T5 longer than that of C1) and to noticeably improve the processability of the composition (much lower Mooney value than for composition C1, 30% lower than that of C1).

It may be noted that composition C2, not comprising any coupling agent in accordance with the invention, also has a better scorch safety relative to composition C1. However, it is difficult to capitalize on this scorch safety property given the high value of the Mooney plasticity of composition C2 (which makes it difficult to process in the uncured state).

Furthermore, observation of the properties of these compositions after curing shows that, quite remarkably, composition C3 comprising, as coupling agent, an organosilane in accordance with the invention has a hysteresis that on the whole is equivalent to that of the control composition C1, unlike composition C2 for which a large increase in hysteresis is observed (high values of $\tan(\delta)_{max}$ and $\Delta G^*$). The hysteresis is a recognized indicator of the rolling resistance of tires; the lower the hysteresis is, the lower the rolling resistance and consequently the lower the energy consumption of motor vehicles fitted with such tires.

It clearly appears that a composition comprising, as coupling agent, an organosilane of formula (I) in accordance with the invention makes it possible to obtain properties that are equivalent, or even improved (processability, scorch safety) relative to the control standard composition.

It may furthermore be noted that the use of an organosilane in accordance with the invention is particularly advantageous from the point of view of the environment. Specifically, it makes it possible to dispose of the problem of the release of VOCs (volatile organic compounds). Indeed, the organosilane in accordance with the invention does not possess any alkoxyl groups (such as the ethoxyl groups of TESPT or of TESPD) that are the source of the release of alcohol (ethanol in the case of TESPT and TESPD), both during the manufacture of the rubber compositions themselves and during the curing of rubber articles incorporating these compositions.

III-3.1 Test 2

The purpose of this test is to demonstrate the improved properties of zinc-free rubber compositions comprising an organosilane in accordance with the invention as coupling agent, in comparison with rubber compositions that are free of zinc but that use coupling agents conventionally used in rubber compositions for tyre treads having silica as the reinforcing filler.

For this, four compositions based on a diene elastomer (SBR/BR blend), reinforced with a highly dispersible silica (HDS) are prepared, these compositions differing essentially in the following technical characteristics:

composition C1 is a control "standard" composition containing zinc (1.5 phr of ZnO) and the compound TESPT (trade name: "Si69") as coupling agent, identical to that from Test 1, composition C'1 corresponds to composition C1 but is free of zinc, composition C'2 is a composition that is free of zinc and comprises the compound TESPD (trade name: "Si266") as coupling agent, composition C'3 is free of zinc and comprises an organosilane in accordance with the invention: (3-(octyldisulphanyl)propyl)methylsilanediol, as coupling agent.

In order for the properties of compositions C1 and C'1 to C'3 to be comparable, the coupling agents of compositions C'1 to C'3 are used at a content that is isomolar in silicon compared to the control composition C1.

Tables 3 and 4 give the formulation of the various compositions (Table 3—content of the various products expressed in phr or parts by weight per hundred parts of elastomer) and also their properties before curing.

As expected, it is observed on reading Table 4 that eliminating zinc from composition C'1 results in a decrease in the processability (increase in the Mooney value) and a reduction in the scorch time T5, and therefore in the scorch safety, compared to the control composition C1.

Composition C'2 has an acceptable scorch time T5, but an unacceptable decrease in the processability (considerable increase in the Mooney value).

On the other hand, quite astonishingly, it is observed that composition C'3 comprising, as coupling agent, an organosilane in accordance with the invention has not only a scorch time that is identical to the control composition C1 which comprises zinc in a customary amount, but also a processability that is greatly improved compared to this same composition.

It clearly appears that a composition comprising, as coupling agent, an organosilane of formula (I) in accordance with the invention makes it possible to obtain properties in the uncured state that are equivalent, or even improved relative to the control standard composition, without using zinc, unlike compositions comprising other coupling agents, including organosilane disulphides that have a different formula to that of the invention.

It will be noted that the use of an organosilane in accordance with the invention is particularly advantageous from the point of view of the environment with respect to the problem of the release of VOCs mentioned in Test 1 and with respect to the possibility of eliminating zinc from the vulcanization system of a rubber composition without degrading the properties of this composition.

TABLE 1

| | Composition No. | | |
| --- | --- | --- | --- |
| | C1 | C2 | C3 |
| SBR (1) | 70 | 70 | 70 |
| BR (2) | 30 | 30 | 30 |
| Silica (3) | 80 | 80 | 80 |
| coupling agent (4) | 6.4 | — | — |
| coupling agent (5) | — | 5.8 | — |
| coupling agent (6) | — | — | 7.2 |
| carbon black (7) | 5 | 5 | 5 |
| MES oil (8) | 6 | 6 | 6 |
| plasticizing resin (9) | 20 | 20 | 20 |
| DPG (10) | 1.5 | 1.5 | 1.5 |
| anti-ozone wax (11) | 1.5 | 1.5 | 1.5 |
| ZnO (12) | 1.5 | 1.5 | 1.5 |
| antioxidant (13) | 2 | 2 | 2 |
| stearic acid (14) | 2 | 2 | 2 |

TABLE 1-continued

| | Composition No. | | |
|---|---|---|---|
| | C1 | C2 | C3 |
| sulphur | 1 | 1 | 1 |
| accelerator (15) | 2 | 2 | 2 |

(1) SSBR with 25% of styrene, 59% of 1,2-polybutadiene units and 20% of trans-1,4-polybutadiene units ($T_g = -24°$ C.); content expressed as dry SBR (SBR extended with 9% of MES oil, i.e. a total of SSBR + oil equal to 76 phr);
(2) BR (Nd) with 0.7% of 1,2-; 1.7% of trans-1,4-; 98% of cis-1,4- ($T_g = -105°$ C.);
(3) "ZEOSIL 1165 MP" silica from Rhodia in the form of micropearls (BET and CTAB: around 150-160 m²/g);
(4) TESPT ("SI69" from Evonik-Degussa);
(5) TESPD ("Si266" from Evonik-Degussa);
(6) (3-(octyldisulphanyl)propyl)methylsilanediol (synthesized product);
(7) N234 (Evonik-Degussa);
(8) MES oil ("Catenex SNR" from Shell);
(9) polylimonene resin ("Dercolyte L120" from DRT);
(10) diphenylguanidine (Perkacit DPG from Flexsys);
(11) mixture of macrocrystalline and microcrystalline anti-ozone waxes;
(12) zinc oxide (industrial grade - Umicore);
(13) N-1,3-dimethylbutyl-N-phenyl-para-phenylenediamine ("Santoflex 6-PPD" from Flexsys);
(14) stearine ("Pristerene 4931" - Uniqema);
(15) N-cyclohexyl-2-benzothiazylsulphenamide ("Santocure CBS" from Flexsys).

TABLE 2

| | Composition No. | | |
|---|---|---|---|
| | C1 | C2 | C3 |
| Properties before curing | | | |
| Mooney (MU) | 93 | 121 | 65 |
| T5 (min) | 21 | >30 | >30 |
| Properties after curing | | | |
| ΔG* (MPa) | 4.75 | 5.75 | 4.48 |
| tan(δ)$_{max}$ | 0.361 | 0.389 | 0.374 |

TABLE 3

| | Composition No. | | | |
|---|---|---|---|---|
| | C1 | C'1 | C'2 | C'3 |
| SBR (1) | 70 | 70 | 70 | 70 |
| BR (2) | 30 | 30 | 30 | 30 |
| Silica (3) | 80 | 80 | 80 | 80 |
| coupling agent (4) | 6.4 | 6.4 | — | — |
| coupling agent (5) | — | — | 5.8 | — |
| coupling agent (6) | — | — | — | 7.2 |
| carbon black (7) | 5 | 5 | 5 | 5 |
| MES oil (8) | 6 | 6 | 6 | 6 |
| plasticizing resin (9) | 20 | 20 | 20 | 20 |
| DPG (10) | 1.5 | 1.5 | 1.5 | 1.5 |
| anti-ozone wax (11) | 1.5 | 1.5 | 1.5 | 1.5 |
| ZnO (12) | 1.5 | — | — | — |
| antioxidant (13) | 2 | 2 | 2 | 2 |
| stearic acid (14) | 2 | 2 | 2 | 2 |
| sulphur | 1 | 1 | 1 | 1 |
| accelerator (15) | 2 | 2 | 2 | 2 |

TABLE 4

| | Composition No. | | | |
|---|---|---|---|---|
| Properties before curing | C1 | C'1 | C'2 | C'3 |
| Mooney (MU) | 93 | 97 | 129 | 64 |
| T5 (min) | 21 | 11 | 18 | 22 |

The invention claimed is:

1. The organosilane of general formula I below:

$$(HO)_2R^1Si-Z-S_m-R^2$$

wherein:
R$^1$ represents a monovalent hydrocarbon-based group chosen from alkyls, which are linear or branched, cycloalkyls or aryls, having from 1 to 18 carbon atoms;
R$^2$ represents a monovalent hydrocarbon-based group chosen from alkyls, which are linear or branched, cycloalkyls or aryls, having from 1 to 30 carbon atoms;
Z represents a divalent bonding group comprising from 1 to 18 carbon atoms; and
m is a number greater than or equal to 2.

2. The organosilane according to claim 1, wherein m is equal to 2.

3. The organosilane according to claim 1, wherein Z contains one or more heteroatoms chosen from O, S and N.

4. The organosilane according to claim 1, wherein:
R$^1$ is chosen from methyl, ethyl, n-propyl and isopropyl; and
Z is chosen from C$_1$-C$_{18}$ alkylenes and C$_6$-C$_{12}$ arylenes.

5. The organosilane according to claim 4, wherein Z is chosen from C$_1$-C$_{10}$ alkylenes.

6. The organosilane according to claim 5, wherein Z is chosen from C$_1$-C$_4$ alkylenes.

7. The organosilane according to claim 4, wherein R$^1$ is a methyl.

8. The organosilane according to claim 4, wherein R$^2$ is chosen from alkyls having from 1 to 18 carbon atoms.

9. The organosilane according to claim 8, wherein R$^2$ is an octyl.

10. The organosilane according to claim 4, wherein m is equal to 2, R$^1$ is a methyl, R$^2$ is an octyl and Z is a propylene.

11. A process for obtaining an organosilane according to claim 1, wherein the process comprises the steps of:
added to a diazodicarboxylate is a mercaptan of formula (II):

$$R^2-SH,$$

in which R$^2$ has the same meaning as in formula (I),
in order to form a thiohydrazine,
the thiohydrazine obtained is substituted with a second mercaptan of formula (III):

$$(R^3O)_2R^1Si-Z-SH,$$

in which:
R$^1$ and Z have the same meaning as in formula (I),
R$^3$, which are identical or different, represent a monovalent hydrocarbon-based group chosen from alkyls having from 1 to 6 carbon atoms, preferably having from 1 to 3 carbon atoms,
a hydrolysis is carried out in an acid medium that makes it possible to result in the targeted organosilane of formula (I).

12. A method of making a rubber composition comprising coupling a reinforcing inorganic filler and a diene elastomer in the presence of an organosilane according to claim 1.

13. The organosilane according to claim 1, wherein:
R$^1$ is chosen from methyl and ethyl; and
Z is chosen from C$_1$-C$_{18}$ alkylenes and C$_6$-C$_{12}$ arylenes.

* * * * *